United States Patent [19]

Erpenbach et al.

[11] Patent Number: 4,892,971

[45] Date of Patent: Jan. 9, 1990

[54] PROCESS FOR THE PREPARATION OF N-ACETYLPHENYLALANINE

[75] Inventors: Heinz Erpenbach, Cologne; Klaus Gehrmann; Peter Hörstermann, both of Erftstadt, all of Fed. Rep. of Germany

[73] Assignee: Hoechst Aktiengesellschaft, Frankfurt am Main, Fed. Rep. of Germany

[21] Appl. No.: 257,715

[22] Filed: Oct. 14, 1988

[30] Foreign Application Priority Data

Oct. 30, 1987 [DE] Fed. Rep. of Germany ..... 37368613

[51] Int. Cl.$^4$ .............................................. C07C 99/06
[52] U.S. Cl. .................................................. 562/450
[58] Field of Search .................. 562/450, 443; 508/396

[56] References Cited

U.S. PATENT DOCUMENTS

| | | | |
|---|---|---|---|
| 2,449,191 | 9/1948 | Behrens | 562/450 |
| 3,574,763 | 4/1971 | Wollner et al. | 568/396 |
| 4,508,921 | 4/1985 | Amato et al. | 562/561 |
| 4,535,167 | 8/1985 | Freidinger | 562/450 |
| 4,612,388 | 9/1986 | Mita et al. | 562/450 |
| 4,613,691 | 9/1986 | Mirviss et al. | 562/450 |
| 4,675,439 | 6/1987 | Mita et al. | 562/450 |

FOREIGN PATENT DOCUMENTS 748239  4/1956  United Kingdom ............... 568/396

*Primary Examiner*—James H. Reamer

[57] ABSTRACT

In the process for the preparation of N-acetylphenylalanine by opening the ring of 2-methyl-4-benzylidene-1,3-oxazolin-5-one with water to give 2-acetaminocinnamic acid and subsequently catalytically hydrogenating the latter, both reaction stages are carried out in a mixture of an aliphatic $C_3$-ketone to $C_{10}$-ketone or a water-miscible ether and water as the solvent, and the hydrogenation of the 2-acetaminocinnamic acid is carried out at temperatures of 10° to 50° C. and pressures of 1 to 15 bar in the presence of a supported palladium catalyst.

3 Claims, No Drawings

PROCESS FOR THE PREPARATION OF N-ACETYLPHENYLALANINE

The invention relates to a process for the preparation of N-acetylphenylalanine by opening the ring of 2-methyl-4-benzylidene-1,3-oxazolin-5-one with water to give 2-acetaminocinnamic acid and subsequent catalytic hydrogenation of the latter.

2-Methyl-4-benzylidene-1,3-oxazolin-5-one is obtainable, in turn, from benzaldehyde and N-acetylglycine. The reactions are illustrated by means of the following equations:

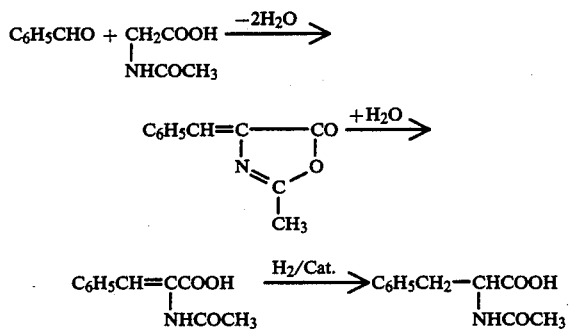

(compare Organic Synthesis, Coll. Vol. 2 (1943), pages 1 to 3 and 491 to 493).

Ring opening and catalytic hydrogenation require working in an organic solvent. Acetone/water mixtures, but also water-miscible ethers, such as tetrahydrofuran, dioxane and ethylene glycol dimethyl ether, are mentioned for the ring opening. Alcohol/water mixtures have proved particularly suitable for the catalytic hydrogenation.

It would be a considerable simplification for the process of preparing N-acetylphenylalanine if both the ring opening and the hydrogenation could be carried out in one and the same solvent.

For the ring opening with water the organic solvent must be miscible with water. Alcohols are unsuitable, since they can react with the 2-methyl-4-benzylidene-1,3-oxazolin-5-one ring with the formation of esters (compare Synthesis, December 1983, pages 1041 to 1043). On the other hand, it appears to be impossible to carry out catalytic hydrogenation in acetone or acetone/water mixtures, since there is a possibility of the acetone being hydrogenated (Houben-Weyl, Methoden der Organischen Chemie ("Methods of Organic Chemistry"), Volume 4, Part 1C, (1980), pages 192 et seq.).

Surprisingly, however, it has been found that hydrogenation of the double bond in the 2-acetaminocinnamic acid to give acetylphenylalanine is also possible in acetone/water mixtures, without hydrogenation of the acetone resulting, within a specific range of temperature and pressure, under mild conditions and in the presence of a specific catalyst. This makes it possible to carry out ring opening and catalytic hydrogenation without changing the solvent, which not only means a simplification in regard to the process, but also a considerable increase in yield, since it is possible to dispense with intermediate isolation of the N-acetaminocinnamic acid.

In detail the process of the invention now comprises carrying out the two reaction stages in a mixture of an aliphatic $C_3$-ketone to $C_{10}$-ketone or a water-miscible ether and water as the solvent, and carrying out the hydrogenation of the 2-acetaminocinnamic acid at temperatures of 10° to 50° C. and pressures of 1 to 15 bar in the presence of a supported palladium catalyst.

The process of the invention can also preferably and optionally comprise:
(a) employing mixtures of acetone and water as the solvent;
(b) employing mixtures of tetrahydrofuran, dioxane or ethylene glycol dimethyl ether and water as the solvent; and
(c) employing a solvent mixture containing 5 to 50% by weight of water.

The procedure in general is to split 2-methyl-4-benzylidene-1,3-oxazolin-5-one to give 2-acetaminocinnamic acid by heating in water/acetone mixtures, and then to add the supported palladium catalyst to the reaction solution and to hydrogenate with hydrogen. The N-acetylphenylalanine obtained from the reaction solution is used, for example, for the preparation of phenylalanine.

The supported palladium catalyst can contain 0.5 to 10% by weight of palladium. Examples of suitable supports are silica gel, activated charcoal, aluminum oxide and barium sulfate. The catalytic hydrogenation is preferably carried out in a pressure range from 1 to 10 bar and at temperatures of 15° to 50° C. The amount of supported catalyst to be employed can vary within wide ranges, but for reasons of cost alone, a small amount is preferable. Ketone/water mixtures, in particular acetone/water mixtures, are preferred as the solvent for both stages of the reaction over water-miscible ethers, because they can be handled more easily and also for reasons of cost.

EXAMPLE 6 kg of 2-methyl-4-benzylidene-1,3-oxazolin-5-one are dissolved in 58 kg of acetone and heated to reflux temperature. 32 kg of water are then added, and the mixture is heated under reflux for 3 hours. The mixture is cooled, 2.69 kg of a supported Pd catalyst (support: silica gel; 1.5% by weight of Pd) are added, the mixture is flushed with nitrogen and treated with hydrogen and hydrogenation is carried out at 30° C. and a pressure of 2 bar. When the theoretical amount of hydrogen has been taken up, the mixture is cooled, the catalyst is filtered off and the mixture of solvents is removed. The yield of N-acetylphenylalanine is 95% of theory.

We claim:
1. A process for the preparation of N-acetylphenylalanine from 2-methyl-4-benzylidene-1,3-oxazolin-5-one, which process comprises:
   opening the ring of the 2-methyl-4-benzylidene-1,3-oxazolin-5-one with a ring-opening agent consisting essentially of water in a solvent medium which is a mixture consisting essentially of said water and an aliphatic $C_3$-ketone to $C_{10}$-ketone or a water-miscible ether, thereby obtaining 2-acetaminocinnamic acid in said solvent medium,
   hydrogenating the resulting 2-acetaminocinnamic acid in said solvent medium at a temperature in the range of 10° to 50° C. and at a pressure of 1 to 15 bar in the presence of a supported palladium catalyst, thereby obtaining the N-acetylphenylalanine.
2. The process as claimed in claim 1, wherein said solvent medium consists essentially of a mixture of acetone and water or a mixture of tetrahydrofuran, dioxane, or ethylene glycol dimethyl ether and water.
3. The process as claimed in claim 2, wherein the amount of said water is 5 to 50% by weight of the mixture.